United States Patent [19]

McAlister et al.

[11] Patent Number: 5,969,261

[45] Date of Patent: *Oct. 19, 1999

[54] APPARATUS AND METHOD FOR MEASURING RUTTING SUSCEPTIBILITY

[75] Inventors: Donald K. McAlister, Apex; John T. Eagan, Jr., Cary, both of N.C.

[73] Assignee: Troxler Electronics Laboratories, Inc., Research Traingle Park, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/634,285

[22] Filed: Apr. 18, 1996

Related U.S. Application Data

[63] Continuation of application No. 08/583,998, Jan. 11, 1996, abandoned.

[51] Int. Cl.[6] .................................................. G01M 17/02
[52] U.S. Cl. .............................................. 73/813; 73/146
[58] Field of Search ............................... 73/7–10, 865.6, 73/813, 815, 825, 818, 146, 841

[56] References Cited

U.S. PATENT DOCUMENTS 5,641,901   6/1997   Powell ...................................... 73/146

OTHER PUBLICATIONS

CPN International brochure featuring Rutmeter, 2 pages (date unknown).

Tim Aschenbrener, "Evaluation of the Hamburg Wheel Tracking Device to Predict Moisture Damage in Hot Mix Asphalt", Transporation Research Board, Paper No. 950475, Jan. 1995.

James S. Lai and Thay–Ming Lee, "Use of a Loaded–Wheel Testing Machine To Evaluate Rutting of Asphalt Mixes"; Transportation Research Record 1269, 116–124.

Timothy Aschenbrener, et al.; "Comparison of the Hamburg Wheel Tracking Device and the Environmental Conditioning System to Pavements of Known Stripping Performance", FHWA Report CDOT–DTD–R–94–1, Jan. 1994.

James S. Lai, "Development of a New Loaded Wheel Testing Machine for Evaluating Rutting of Asphalt Mixes", GDOT Research Project 9201, Sep., 1993.

Robert Collins, et al., "Development and Use of the Georgia Loaded Wheet Tester", Transportation Research Board, Paper No. 950992, Jan. 1995.

Tyler Miller, et al., "Utilizing the Georgia Loaded Wheel Tester to Predict Rutting", Transportation Research Board, Paper No. 950520, Jan. 1995.

Tim Aschenbrener and Keith Stuart, "Description of Demonstration of European Testing Equipment for Hot Mix Asphalt Pavement", FHWA Report CDOT–DTD–R–92–10, Oct., 1992.

*Primary Examiner*—Robert Raevis
*Attorney, Agent, or Firm*—Alston & Bird LLP

[57] ABSTRACT

An apparatus and method for testing rutting susceptibility of test specimens. The apparatus includes a specimen holder having cavities for receiving one or more test specimens having an exposed surface for testing. A load bearing surface is positioned above the specimens to prevent friction from effecting the rutting analysis. A load device including at least one loading wheel is positioned adjacent the specimen holder wherein the loading wheels matingly engage the load bearing device. A motive sources provides relative rotational movement between the specimen holder and the loading wheels whereby a load is repeatedly applied to the test specimens under a constant velocity. The method includes testing rutting susceptibility of test specimens by providing a rotational load thereupon whereby the load reflects a linear or constant load across the predetermined path of travel of the loading wheels over the exposed surface of the test specimens.

40 Claims, 2 Drawing Sheets

APPARATUS AND METHOD FOR MEASURING RUTTING SUSCEPTIBILITY

CROSS REFERENCE TO RELATED APPLICATION

This application is a continuation of U.S. application Ser. No. 08/583,998 filed Jan. 11, 1996, now abandoned.

FIELD OF THE INVENTION

The present invention relates to a method and apparatus for measuring the susceptibility of a specimen to damage due to rutting.

BACKGROUND OF THE INVENTION

Rutting on asphaltic pavement has been a significant concern of highway commissions in the United States. Rutting is caused by a load passing repeatedly across the surface of pavement and results in lateral spreading of the pavement from the location of load application, thereby producing a rut or groove. This problem has increased in severity as the wheel loads and truck traffic on highways have increased. Rutting may cause roads and highways to become non-serviceable and dangerous. If excessive, rutting may produce hazardous conditions, such as increasing the likelihood of vehicle hydroplaning due to water accumulating in the formed rut.

Because of these problems and dangers, highway commissions in the United States and throughout strive to install the safest and most economical pavement available. Hence, test specimens of the prospective pavement material must be tested during the developmental stages, i.e., prior to construction, to determine the susceptibility of a given material to damage by rutting.

Various devices and test methods have been proposed for testing asphalt pavement. For instance, U.S. Pat. No. 3,119,257 to Speer is directed to a traffic simulator apparatus and method. The test track of that apparatus is polygonal and is formed of plural elongated, substantially rectangular paving strips joined end to end. A central column including a turntable apparatus from which radially arms extend therefrom are provided wherein each arm retains a wheel, preferably an actual rubber tire. The central column is rotated so the wheels traverse the upper surface of the polygonal track. The apparatus of Speer is extremely large, making it impractical in a laboratory environment.

The Georgia Loaded Wheel Testing Apparatus, developed by James S. Lai, Professor School of Civil and Environmental Engineering, Georgia Institute of Technology with the cooperation of the Georgia Department of Transportation, was initially developed in 1985 and modified in 1992. The Georgia Loaded Wheel Testing Apparatus is a two part system. A compactor creates a compacted hot mix asphalt specimen and a wheel tracking system repeatedly applies a load to the specimen. The wheel tracking system includes a slidable tray for retaining a beam sample tray for holding the samples. The slidable tray is associated with a reciprocating drive assembly. An inflated tube is positioned over the specimen and a weighted wheel is positioned thereover wherein the specimens are rotated to create rutting. The wheels are thus passed in a reciprocating or side to side manner, whereby the time and velocity of the load application across the specimen is sinusoidal. This type of load, however, is dissimilar to actual loads applied to pavement. Furthermore, the reciprocating motion of the specimen is an inefficient use of energy when the motion is driven by a rotating motor.

Other attempts related to asphaltic pavement testing include the Hamburg Wheel Tracking Device manufactured by Helmut-Wind, Inc. of Hamburg, Germany. The Hamburg Device is used to measure moisture sensitivity as well as rutting susceptibility. A weighted steel wheel is rolled back and forth over a compacted specimen which is immersed in water. The rate of deformation is used to determine the susceptibility to water damage, stripping, and rutting. Stripping results from the direct contact of the steel wheel against the surface of the specimen. Like the Georgia Loaded Wheel Tester, the wheels of The Hamburg Device are reciprocated across the surface of the test specimen resulting in a load wherein the time and velocity of the load application upon the specimens is sinusoidal.

These and other prior art approaches have many shortcomings or limitations which significantly restrict their usefulness or practicality as a laboratory test instrument for achieving accurate and reproducible evaluations of the susceptibility of a test specimen to rutting.

SUMMARY OF THE INVENTION

The present invention overcomes the limitations of the prior art and provides an apparatus and method which is well suited for use in a laboratory environment for accurately and reproducibly measuring the susceptibility of test materials, such as asphaltic paving mix, to rutting. The method and apparatus advantageously utilizes test specimens of a compact configuration which can be easily and consistently formed and handled. Load is applied to the test specimen in a manner which simulates actual load conditions to achieve the most accurate and reproducible results.

More particularly, the specimen is supported in a specimen holder having a plurality of cavities circularly arranged about a central axis. Each cavity is configured to receive a test specimen and to laterally support the sides of the test specimen while holding the specimen with a surface exposed for testing. The test specimen is configured such that the path of travel of the load across the exposed surface extends from a first location along the periphery of the specimen to a second peripheral location wherein the shortest distance (i.e., a straight line) between the first and second peripheral locations is no greater than the maximum dimension of the specimen in a direction generally transverse to an axis extending between the peripheral points. A load device is provided for repeatedly applying a load to the exposed surface of the test specimen. The load device comprises a single wheel and a single, pneumatically driven hydraulic load wherein the specimen holder rotates beneath the load device to cause the loading wheel to follow a predetermined path of travel successively across each of the cavities of the specimen holder so as to repeatedly apply load for forming a rut in the test specimens.

Preferably, the specimen is in the form of a cylindrical plug. More particularly, the plug is formed by a gyratory compactor into the plug-shaped configuration. Gyratory compactors are familiar to highway commissions and highway contractors. The testing laboratories of many such commissioner and contractors already use gyratory compactors for evaluating and testing physical properties, such as the compaction characteristics, of pavement materials. An example of one known gyratory compactor apparatus is described in U.S. Pat. No. 5,323,655. The present invention is especially advantageous in that it can utilize the same plug shaped gyratory compacted test specimens that are already being produced by the testing laboratories for performing other tests. As a result, testing for rutting susceptibility can be carried out in a timely and efficient manner in accordance with the present invention. The gyratory compacted plug-shaped specimen (or "gyratory plug") is uniformly compacted into a dense, homogeneous plug which is strong and stable enough to withstand handling and placement into the testing apparatus without damage and without risk of affecting the rutting properties. Indeed, it has been determined that the gyratory compacted plug-shaped specimen used in the present invention produces much more reproducible and dependable test results since the test specimen is more nearly representative of the pavement material as it exists under actual conditions of use.

The method according to the present invention includes the steps of forming a test specimen, positioning the specimen with a surface thereof exposed for testing, and passing a load repeatedly along a predetermined path of travel across the exposed surface of the test specimen to form a rut. The step of forming the test specimen includes forming the specimen in a compact configuration such that the length of the path of travel across the exposed surface of the specimen is no greater than the maximum dimension of the specimen in a direction transverse to the path of travel.

BRIEF DESCRIPTION OF THE DRAWINGS

The foregoing and other features and advantages of the present invention will be made apparent from the following detailed description of a preferred embodiment of the invention and from the drawings, in which.

DETAILED DESCRIPTION

Figure 1:
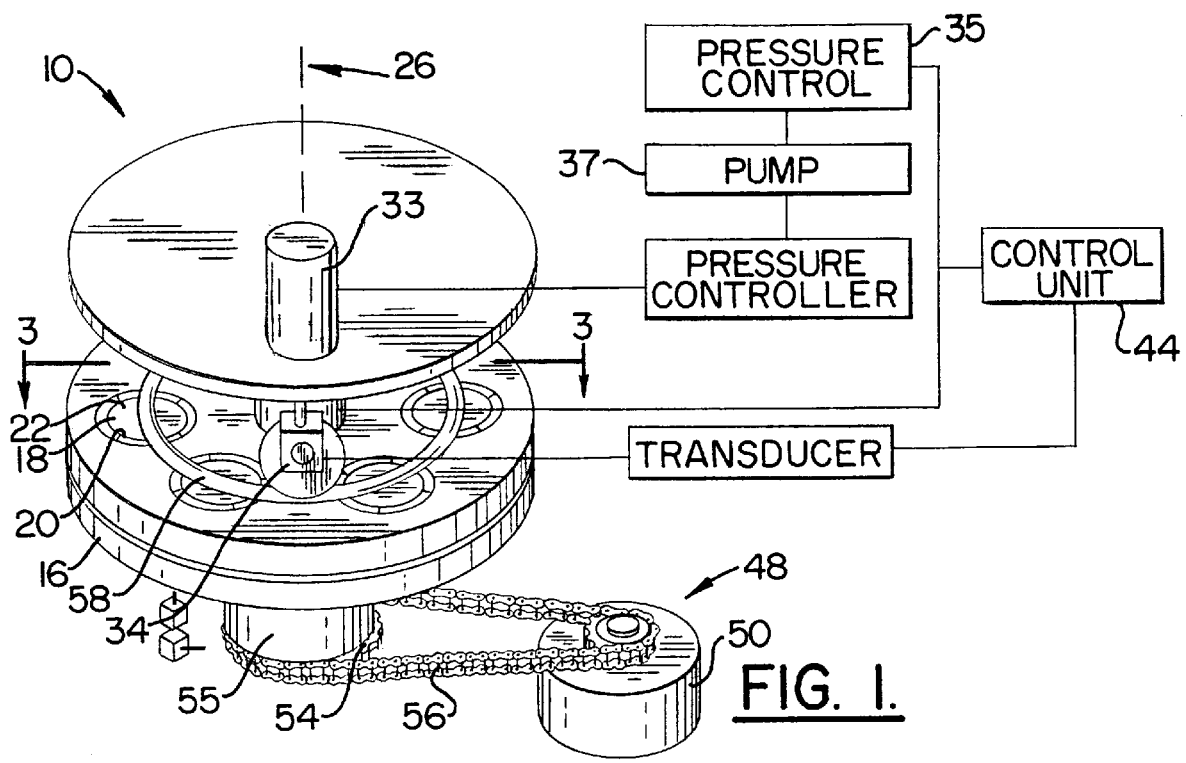
FIG. 1 is a simplified, schematic perspective view of an apparatus according to a first embodiment of the present invention showing the load device and specimen holder.

The present invention will now be described more fully in detail with reference to the accompanying drawings, in which a preferred embodiment of the invention is shown. This invention should not, however, be construed as limited to the embodiment set forth herein; rather, it is provided so that this disclosure will be thorough and complete and will fully convey the scope of the invention to those skilled in the art.

The apparatus for testing the susceptibility of a test specimen to rutting is indicated generally at 10 and includes, generally, an environmentally controlled chamber 12, a load device 14, and a specimen holder 16. The chamber 12 provides constant testing conditions such as, for example, temperature. In a preferred embodiment, the temperature is maintained at approximately 105° F. Constant temperature may be maintained by known heating techniques such as by providing a heating element associated with the control unit 44 (discussed below) and the use of insulated walls (not shown).

The rutting analysis is performed upon a test specimen 18 which is positioned within the specimen holder 16 having a cavity 20 configured to receive the test specimen 18 and to hold the specimen with a surface thereof exposed for testing. The exposed surface 22 shown is the upper surface of the test specimen. A load device 14 is positioned adjacent the specimen holder 16 and cooperates therewith for passing a load repeatedly in the same direction along a predetermined path of travel across the exposed surface 22 of the test specimen 18 to form a rut. In the embodiment shown in the various Figures, the specimen holder 16 includes a plurality of cavities 20 circularly arranged about a central axis indicated generally at 26, with each cavity 20 being configured to receive a test specimen 18. The specimens 18 are separated a predetermined distance. It is within the scope of the invention to provide the specimens 18 immediately adjacent one another wherein a portion of adjacent specimens are in contact with one another.

Each cavity 20 has walls 28 located on at least the opposite sides of the predetermined path of travel for engaging the specimen and providing lateral support thereto during testing. Moreover, as shown, each cavity has a cylindrical configuration corresponding to the cylindrical shape of the test specimen 18 and the walls thus support the test specimen along its entire circumference. It is, however, within the scope of the present invention to employ test specimens 18 and correspondingly configured specimen holders 16 of various geometric configurations. The specimen holder 16 rests upon a bearing 17 which allows it to rotate freely. The base 19 of the specimen holder is firmly supported to prevent movement that might interfere with the rutting analysis.

While any material may be used to form the test specimen 18, in a preferred embodiment the test specimen 18 comprises bituminous paving material. The specimen may be formed in any manner, but in a preferred embodiment, it is formed by gyratory compaction into the form of a cylindrical "gyratory plug" as set forth in U.S. Pat. No. 5,323,655 to Eagan et al., which is incorporated herein by reference. A specimen formed according to the '655 patent is preferred because of its substantial benefits. The gyratory compacted specimens are relatively small and easy to manipulate and analyze. The specimens have known characteristics which are highly reproducible. Additionally, the specimens formed according to the '655 patent most closely resemble actual installed asphaltic pavement. Specimens compacted with a gyratory compactor have been shown to correlate closely with core samples from actual highway pavements in terms of properties such as density and aggregate orientation which may affect rutting. Further, rut testing can be performed on a gyratory compacted specimen which has undergone prior analysis such as compaction performance, thereby avoiding the preparation of another specimen. It is, however, within the scope of the present invention to utilize plugs, cylindrical or non-cylindrical, formed of other paving materials such as, for example, utilizing an actual road plug as the core material for the test specimen 18.

The test specimen 18 shown is of a compact configuration such that the path of travel extends from a first location along the periphery of the specimen to a second peripheral location along the exposed surface 22 of the test specimen 18. The shortest distance between the first and second peripheral locations is no greater than the maximum dimension of the specimen measured along its surface in a direction transverse to an axis (measured along its surface) extending between the peripheral locations. In addition to providing more convenient handling, this feature of the specimen 18 enhances achieving accurate results. Because the dimension of the specimen 18 measured in the direction transverse to the axis extending between the peripheral locations is at least substantially the same as, or more than, the dimension of the specimen 18 measured in the direction of the axis between the peripheral locations, sufficient lateral support is provided for forming a rut. If this were not the case, such as when an extremely long (in the direction of load passage) and relatively narrow specimen were provided, spreading of the specimen material would be less accurate as the material would have more inherent strength in the lengthwise direction than in the transverse direction.

Figure 2:
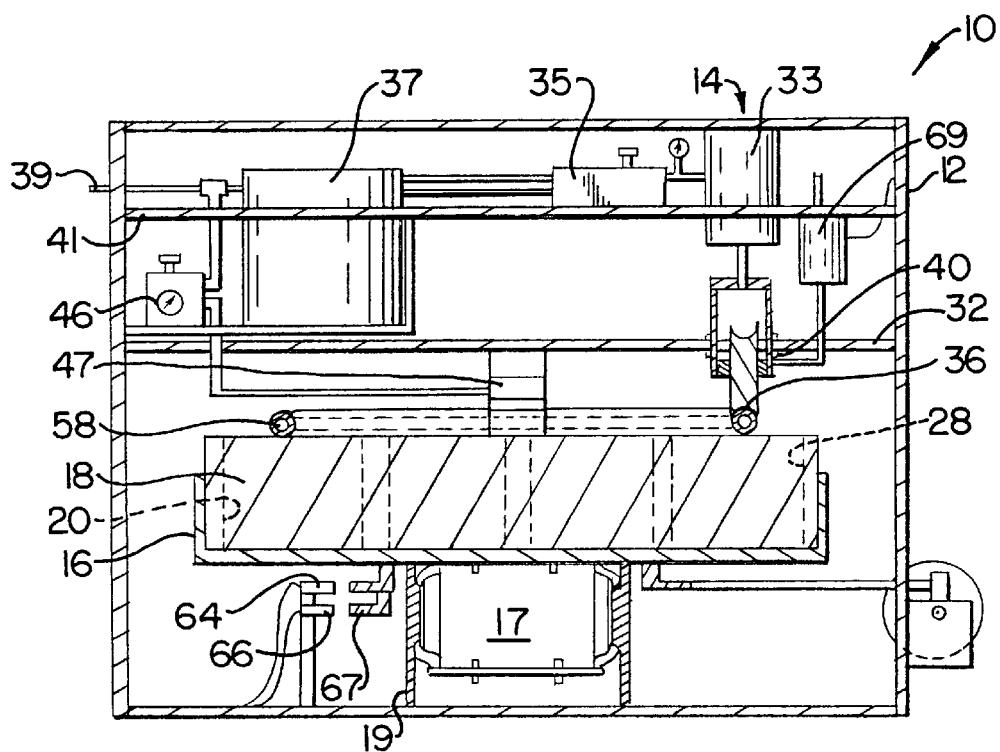
FIG. 2 is a cross sectional view of the apparatus of FIG. 1 in greater detail.
Figure 3:
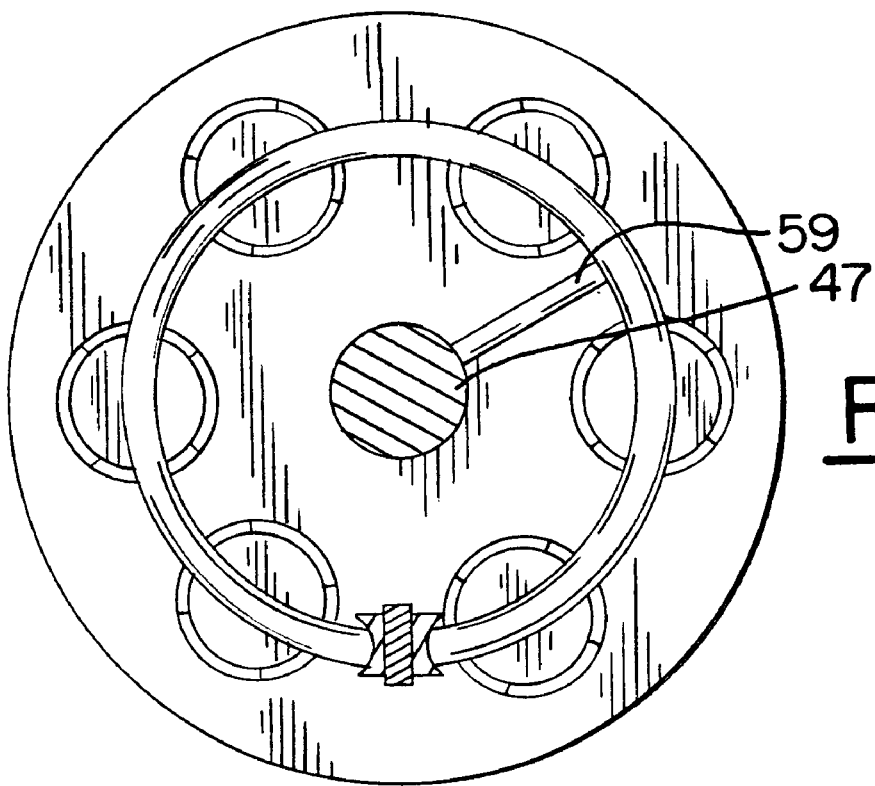
FIG. 3 is a cross sectional view taken at line 3—3 of FIG. 1 showing the specimen holder.

As shown in FIGS. 1–3, the present invention includes the single load device 14 and the single loading wheel 34. The loading wheel 34 is positioned adjacent the specimen holder 16 for applying a load to the exposed surface 22 of the test specimens 18 positioned with the specimen holder 16. The load device 14 includes a loading piston 33 associated with the pressure control 35 for applying pneumatic pressure produced by the pump 37 or air supply to the loading wheel 34. For purposes of illustration, the wheel support plate 32 is not shown in FIG. 1. The pressure controller 35 is associated with the control unit 44 to provide an automated testing apparatus. The pump 37 is pneumatically driven with the port 39 for supplying the pressure to the testing apparatus 10. The piston support plate 41 provides support for the loading piston 33 wherein any load applied to the loading wheel is a result of the pressure from the pump 37. The pressure applied to the loading wheel by the loading piston 33 is measured and monitored by the pneumatic pressure control 35. It is within the scope of the present invention, however, to provide any number of loading wheels and any number of load devices. For instance, a plurality of loading wheels may be provided and associated with either a single load device or a plurality of load devices.

The apparatus 10 for testing the rutting susceptibility of a test specimen 18 further includes means, shown generally at 48, for providing relative movement about the central axis 26 between the specimen holder 16 and the load device 14. This relative movement causes the loading wheel 34 to follow a predetermined path of travel in one direction successively across each of the cavities 20 of the specimen holder 18 so as to repeatedly apply load to the exposed surfaces 22 of the test specimens 18 for forming a rut therein. As shown, the means 48, for providing relative movement imparts rotational movement to the specimen holder 16, preferably at a uniform velocity, while the load device 14 remains substantially stationary against rotation and shifting. However, the opposite relationship could be utilized, if desired. In the embodiment shown, a motive means or source in the form of a motor 50 drives a step-down gearing mechanism. The gearing mechanism includes a gear 54 carried by a shaft 55 which extends downwardly from and is fixed to the specimen holder 16 and the chain 56 engages the gear 54 and a sprocket attached to the shaft of the motor 50. Alternatively, any means known in the art to provide relative movement between the load device and the specimen holder may be used without departing from the present invention.

A load bearing surface in the form of a tube 58 is positioned between the load device 14 and the exposed surface 22 of the specimens 18 for preventing friction therebetween. As seen in the various Figures, the tubular load bearing surface 58 rests above the specimens 18 and is permitted to rotate with the specimen holder 16. The internal pressure of the tube is maintained constant such as by the air pressure control 46 monitored and controlled by the control unit 44. In the embodiments illustrated, a pneumatic tube 58 is selected but any fluid source, such as air or hydraulic fluid, may provide the appropriate internal pressure to provide a substantially frictionless interface between the loading wheel 34 and the specimens 18 with rigidity similar to that of tires of most trucks. In the embodiment shown, a pneumatic line 59 is connected to the air pressure control 46 by a rotating connection 47 supported by wheel support plate 32 at the center of rotation 26 to allow for continuous maintenance of the pressure. Alternatively, once the desired pressure is attained within the tube 58, the tube may be sealed and disconnected from the pressure source.

The loading wheel 34 has a concave surface 36 with a radius generally corresponding to that of the annular load bearing surface 58 to permit the loading wheel 34 to freely receive a portion of the load bearing surface 58. The loading wheel 34 rotates freely upon a bearing 40 associated with the loading wheel support member 32 and each is confined from shifting or cocking during operation. Thus, relative movement between the load device 14 and the specimen holder 16 permits the loading wheels 34 to traverse a surface of the tube 58. As shown, a tube having a circular cross section is used, but an alternative embodiment (not shown) includes a tube having a square cross section. Of course, any configuration may be utilized and the surface 36 of the loading wheel 34 would conform thereto.

In a preferred embodiment, the tube 58 is approximately one inch in diameter. The tube 58 is confined laterally to prevent it from shifting on the specimens 18 during testing. The confinement desirably is loose in the vertical direction to ensure that loading onto the specimen is not affected. Of course, the loading wheels 34 may provide adequate confinement of the load bearing surface 58.

In an alternative embodiment (not shown), the specimen holder 16 may include grooves in its upper surface to correspond with and receive a portion of the tube 58 to further ensure proper rut formation. When a substantial rut has been formed within the upper surface 22 of the test specimen 18, the load bearing surface 58 will rest substantially flat upon the specimen 18 due to the positioning of the grooves. To facilitate this, a biasing member may be provided to vertically support the load bearing surface 58 to enable it to fall within a formed rut. Thus, the strength of the biasing member, preferably in the form of a spring, will be substantially equal to the load applied by the load device 14 and may be adjustable.

The apparatus 10 also comprises sensing means including a gear tooth sensor for controlling the speed and for measuring the position of rotation of the loading device 14 relative to the specimen holder 16 and a once-per revolution sensor 66 determining the rotational position of the specimen. A third sensor 69 for measuring the position of the loading wheel is provided. In the embodiment shown, the third sensor is a linear displacement transducer, although any sensing means may be employed. Each sensor 64 and 66 communicates with the control unit 44 which, by detecting the position of rotation and the position of each specimen, may average the readings taken of each specimen 18 to establish a once per revolution depth of rut for each specimen measured at its center. This information is stored and available for printing or downloading to a computer. The rate of rotation may be controlled by the control unit 44 by a gear tooth sensor 64 and the once per rotation sensor 66.

The operation of the apparatus will now be described in detail. As shown in the various Figures, six test specimens 18 are positioned within a respective cavity 20 of the specimen holder 16. Once the specimens 18 are received within the specimen holder 16, the load bearing surface 58 is placed over the exposed surfaces 22 of the test specimens 18. The load device 14 is then positioned adjacent the tube 58 and hence the exposed surfaces 22 of the test specimens 18 so that the loading wheel 34 or loading wheels 34 are positioned for mating engagement with the tube 58. The control unit 44 regulates the internal pressure of the load bearing surface 58 through the air pressure control 46 extending through the central axis 26 of the load device 14. A predetermined load is then applied by the loading device 14 and hence to the respective loading wheel 34 or wheels 34. The motor 50 is activated to impart relative movement between the load device 14 and the exposed surface 22 of the specimens 18 to produce rutting. After the rutting test has been performed, the test specimen 18 may be utilized for performance of a task different than rutting.

Because the velocity of the load, and hence the amount of time the load is applied at any location of the specimen, is constant along the predetermined path of travel, the wear rate across the specimen 18 is constant. Of course, a non-homogeneous material or a poor sampling of material may result in a less than constant wear rate but the apparatus of the present invention ensures that any uneven wear is the result of problems in the specimen. This contrasts with prior art devices which are reciprocated back and forth across test specimens, thereby applying a load wherein the time and velocity of the load application reflects a sinusoidal function, i.e., wherein the speed of travel of the load is greater in the center than at each of the ends along the predetermined path of travel.

While only preferred embodiments have been shown in the various Figures, the present invention is not thereto limited. For example, the pressure or load may be applied through the specimen holder rather than through the loading wheels 34 of the load device 14. Moreover, the load device 14 may rotate while the specimen holder 16 does not. The specimens 18 may be placed in a water bath and the device may be used for determining water damage and stripping in addition to rutting. The specimens may be confined within the cavities 20 of the specimen holder 16 by set screws or other clamping mechanisms. In another embodiment (not shown), each of the wheels 34 may comprise an independent means for applying a load thereto. Additionally, the loading wheels 34 may not be freely rotatable.

While particular embodiments of the invention have been described, it will be understood, of course, the invention is not limited thereto since modifications may be made by those skilled in the art, particularly in light of the foregoing teachings. It is, therefore, contemplated by the appendant claims to cover any such modifications that incorporate those features of these improvements in the true spirit and scope of the invention.

That which is claimed is:

1. An apparatus for testing the susceptibility of a test specimen to rutting comprising: a test specimen; a specimen holder having a cavity configured to receive said specimen and to hold the specimen with a surface thereof exposed for testing; and a load device positioned adjacent said specimen holder and cooperating therewith for passing a load repeatedly in only one direction along a predetermined path of travel along the exposed surface of the test specimen to form a rut; said test specimen being of a compact configuration and said path of travel extending from a first peripheral location to a second peripheral location such that the shortest distance between said peripheral locations along the exposed surface of the specimen is no greater than the maximum dimension of the specimen in a direction transverse to an axis extending between said peripheral locations.

2. An apparatus according to claim 1, wherein said load is a repeating load.

3. An apparatus according to claim 2, wherein said specimen holder has a plurality of cavities configured to receive respective specimens and to hold the specimens with a surface thereof exposed for testing.

4. An apparatus according to claim 3, wherein said cavities of said specimen holder are of a cylindrical configuration, and said specimens are in the form of cylindrical plugs.

5. An apparatus according to claim 2 wherein said specimen holder is mounted for rotation relative to said load device.

6. An apparatus according to claim 5 further comprising sensor means for measuring the rutting of said test specimen.

7. An apparatus according to claim 6 wherein said sensor means includes a first sensor for measuring the position of rotation of said load device relative to said specimen holder and a second sensor positioned on said load device for measuring the height of said load device as it passes over the test specimen.

8. An apparatus according to claim 2, wherein said specimen holder has walls located on opposite sides of said predetermined path of travel engaging the specimen and providing lateral support thereto during testing.

9. An apparatus according to claim 1, wherein said cavity of said specimen holder has a cylindrical configuration, and said specimen is in the form of a cylindrical plug.

10. An apparatus according to claim 9, wherein said predetermined path of travel extends along an end surface of said cylindrical plug.

11. An apparatus according to claim 1, wherein said specimen comprises bituminous paving material compacted by gyratory compaction into the form of a cylindrical plug.

12. An apparatus according to claim 1 wherein said load device comprises at least one loading wheel arranged for applying the load repeatedly along the predetermined path of travel along the exposed surface of said test specimen.

13. An apparatus according to claim 12 additionally including a load bearing surface interposed between said at least one loading wheel and said exposed surface of said test specimen for applying the load to the exposed surface of said test specimen while preventing friction between said exposed surface of said test specimen and said load device.

14. An apparatus according to claim 13 wherein said load bearing surface comprises a pressurized tube.

15. An apparatus according to claim 12 wherein said at least one loading wheel is associated with a pressure source.

16. An apparatus according to claim 1 further comprising a motive source connected to said apparatus for imparting relative movement between said load device and said test specimen for causing the load to pass repeatedly in the same direction along a predetermined path of travel extending along the exposed surface of the test specimen.

17. An apparatus for testing the susceptibility of a test specimen to rutting comprising:

a specimen holder having at least one cavity defined by walls configured to receive a test specimen, said walls being arranged to laterally support sides of the test specimen along the entire periphery of the test specimen while holding the specimen with a surface thereof exposed for testing;

a load device positioned adjacent said specimen holder for applying a load to the exposed surface of the test specimen; and motive means cooperating with said load device and with said specimen holder for passing the load repeatedly in only one direction along a predetermined path of travel extending along the exposed surface of the test specimen for forming a rut in the test specimen.

18. An apparatus according to claim 17 wherein said motive means is operable for causing the load to pass repeatedly at a uniform velocity along said path of travel across the exposed surface of the specimen.

19. An apparatus according to claim 17 wherein said predetermined path of travel extends across the exposed surface of the test specimen.

20. An apparatus according to claim 18 wherein said at least one cavity has a cylindrical configuration for receiving a gyratory plug of compacted paving material.

21. An apparatus for testing the susceptibility of a test specimen to rutting comprising:
   a specimen holder having a plurality of cavities circularly arranged about a central axis, each cavity configured to receive a test specimen and to laterally support sides of the test specimen while holding the specimen with a surface thereof exposed for testing;
   a loading wheel positioned adjacent said specimen holder for applying a load to an exposed surface of a specimen positioned in said specimen holder;
   means for applying a load to said loading wheel;
   means for rotating said specimen holder about said central axis to cause the loading wheel to follow a predetermined path of travel successively across each of said cavities of said specimen holder for repeatedly applying the load to the test specimens in said specimen holder.

22. An apparatus according to claim 21 further comprising an annular load bearing surface positioned between said loading wheel and said exposed surface of said test specimen and arranged so that the load applied to said loading wheel bears against said load bearing surface as the loading wheel travels successively across each of cavities of said specimen holder.

23. An apparatus according to claim 22 wherein said annular load bearing surface is positioned over each of the plurality of cavities and wherein said loading wheel is configured to be positioned upon at least a portion of said load bearing surface as said loading wheel moves circularly along said load bearing surface.

24. An apparatus according to claim 23 wherein said load bearing surface comprises a pressurized tube, and wherein said tube is maintained at a constant internal pressure.

25. A method for testing the susceptibility of a test specimen to rutting comprising: forming a test specimen; positioning the specimen with a surface thereof exposed for testing; passing a load repeatedly in only one direction along a predetermined path of travel along the exposed surface of the test specimen to form a rut; and wherein said step of forming the test specimen comprises forming the specimen in a compact configuration such that the length of said path of travel along the exposed surface of the specimen is no greater than the maximum dimension of the specimen in a direction transverse to said path of travel.

26. A method according to claim 25 wherein said step of passing the load includes passing the load across the exposed surface of the test specimen.

27. A method according to claim 25 wherein the step of passing a load along a predetermined path of travel across the exposed surface of the test specimen includes repeatedly passing the load across the exposed surface.

28. A method according to claim 27 wherein said step of positioning the specimen comprises positioning the specimen in a holder and holding the specimen with a surface thereof exposed for testing while laterally supporting the specimen on opposite sides of said predetermined path of travel.

29. A method according to claim 25 wherein said step of positioning the specimen comprises positioning the specimen in a holder having a cavity configured to receive said specimen and holding the specimen in the holder during testing with a surface thereof exposed for testing.

30. A method according to claim 29 further comprising the step of moving said holder during testing repeatedly in the same direction along a predetermined path of travel with respect to the load to cause the load to pass repeatedly across the exposed surface of the test specimen.

31. A method for testing the susceptibility of a test specimen to rutting comprising: compacting bituminous paving material by gyratory compaction into the form of a plug; positioning the plug with a surface thereof exposed for testing; and passing a load repeatedly in only one direction along a predetermined path of travel along the exposed surface of the plug to form a rut.

32. A method according to claim 31 wherein said step of passing the load includes passing the load across the exposed surface of the test specimen.

33. A method according to claim 31 further comprising the step of using the same plug and also performing a test different than rutting thereon.

34. A method according to claim 31 further comprising the step of measuring the rut formed on the exposed surface of the test specimen repeatedly after successive passes of the load across the exposed surface.

35. A method for testing the susceptibility of a test specimen to rutting comprising: positioning test specimens within respective circularly arranged cavities of a specimen holder; laterally supporting each test specimen within its respective cavity with end walls while exposing a surface of the test specimen exposed for testing; and applying a load repeatedly to the exposed surface so as to extend between said end walls of each test specimen.

36. A method according to claim 35 wherein said step of applying a load repeatedly to each test specimen comprises positioning a loading wheel adjacent the test specimen, applying a load to the loading wheel, and imparting relative rotational movement between the specimen holder and the loading wheel about a central axis to cause the loading wheel to pass successively across each of the test specimens.

37. An apparatus for testing the susceptibility of a test specimen to rutting comprising: a test specimen; a specimen holder having a plurality of cavities configured to receive respective specimens and to hold the specimen with a surface thereof exposed for testing; and a load device positioned adjacent said specimen holder and cooperating therewith for repeatedly passing a load along a predetermined path of travel across the exposed surface of the at least one test specimen to form a rut, said test specimen being of a compact configuration and said path of travel extending from a first peripheral location to a second peripheral location such that the shortest distance between said peripheral locations across the exposed surface of the specimen is no greater than the maximum dimension of the specimen in a direction transverse to an axis extending between said peripheral locations.

38. An apparatus for testing the susceptibility of a test specimen to rutting comprising:
   a test specimen;
   a specimen holder having a cavity configured to receive said specimen and to hold the specimen with a surface thereof exposed for testing; and
   a load device positioned adjacent said specimen holder and cooperating therewith for repeatedly passing a load along a predetermined path of travel across the exposed surface of the test specimen to form a rut wherein said specimen holder is mounted for rotation relative to said load device, said test specimen being of a compact configuration and said path of travel extending from a first peripheral location to a second peripheral location such that the shortest distance between said peripheral locations across the exposed surface of the specimen is no greater than the maximum dimension of the specimen in a direction transverse to an axis extending between said peripheral locations.

39. An apparatus for testing the susceptibility of a test specimen to rutting comprising: a cylindrical test specimen; a specimen holder having a cylindrical cavity configured to receive said cylindrical test specimen and to hold the specimen with an end surface thereof exposed for testing; and a load device positioned adjacent said specimen holder and cooperating therewith for passing a load repeatedly in only one direction along the exposed surface of the test specimen to form a rut; said load device comprising at least one loading wheel arranged for applying the load repeatedly along said exposed end surface of the test specimen.

40. An apparatus according to claim 39, wherein said specimen comprises bituminous paving material compacted by gyratory compaction into the form of a cylindrical plug.

* * * * *

UNITED STATES PATENT AND TRADEMARK OFFICE
CERTIFICATE OF CORRECTION

PATENT NO. : 5,969,261

DATED : October 19, 1999

INVENTOR(S) : McAlister et al.

It is certified that error appears in the above-identified patent and that said Letters Patent is hereby corrected as shown below:

Title page, item [73], in the Assignee's name, "Electronics" should read --Electronic--.

Title page, Related U.S. Application Data [63], "Jan. 11, 1996" should read --Jan. 10, 1996--.

Title page, [56] References Cited, U.S. PATENT DOCUMENTS, add the following:

| | | |
|---|---|---|
| --5,323,655 | 6/1994 | Eagan et al. |
| 4,887,463 | 12/1989 | Wood |
| 4,781,058 | 11/1988 | Arnberg |
| 4,502,327 | 3/1985 | Scrivener et al. |
| Re. 27,875 | 1/1974 | Swift |
| 3,572,111 | 3/1971 | Johnson |
| 3,483,744 | 12/1969 | Goldberg |
| 3,382,711 | 5/1968 | Scholl |
| 3,350,929 | 11/1967 | Axelson et al. |
| 3,119,257 | 1/1964 | Speer--. |

Signed and Sealed this

Eleventh Day of April, 2000

*Attest:*

Q. TODD DICKINSON

*Attesting Officer*  *Director of Patents and Trademarks*